United States Patent [19]

Nelson et al.

[11] Patent Number: 4,935,570

[45] Date of Patent: Jun. 19, 1990

[54] OLEFIN OLIGOMER SYNLUBE PROCESS

[75] Inventors: Marshall B. Nelson; Matthew J. Lynch; Thomas J. DiLeo, all of Baton Rouge, La.

[73] Assignee: Ethyl Corporation, Richmond, Va.

[21] Appl. No.: 212,019

[22] Filed: Jun. 27, 1988

[51] Int. Cl.$^5$ ............................ C07C 2/00; C07C 2/04
[52] U.S. Cl. ..................................... 585/329; 585/326; 585/525
[58] Field of Search ................ 585/525, 520, 521, 326, 585/329

[56] References Cited

U.S. PATENT DOCUMENTS

| | | | |
|---|---|---|---|
| 4,225,739 | 9/1980 | Nipe et al. | 585/525 |
| 4,308,414 | 12/1981 | Madgavkar et al. | 585/525 |
| 4,417,082 | 11/1983 | Larkin et al. | 585/525 |

Primary Examiner—Chung K. Pak
Attorney, Agent, or Firm—Joseph D. Odenweller

[57] ABSTRACT

Synlubes having a consistently low pour point are made by feeding a promoter (e.g. water, alcohol) at a controlled rate over an extended time period to an α-olefin (e.g. 1-decene) in contact with boron trifluoride.

14 Claims, No Drawings

OLEFIN OLIGOMER SYNLUBE PROCESS

BACKGROUND OF THE INVENTION

Alpha-olefin oligomers and their use as hydraulic fluids and synthetic lubricants (synlubes) are well known. U.S. Pat. No. 2,937,129 reports the oligomerization of $C_{5-14}$ α-olefins using a dialkyl peroxide catalyst to make a synlube. U.S. Pat. No. 3,113,167 describes an α-olefin oligomer process using a titanium halide and an aluminum compound.

The preferred catalysts for making α-olefin oligomers are Friedel Crafts metal halides such as $BF_3$, U.S. Pat. No. 3,149,178. Optimum properties are obtained starting with 1-decene although mixtures of α-olefins have been used, U.S. Pat. No. 3,330,883.

The preferred Friedel Crafts catalyst is $BF_3$. Pure $BF_3$ is not an effective oligomerization catalyst. A small amount of polar compound is necessary as a promoter. U.S. Pat. No. 3,382,291 describes the use of alcohol promoters such as decanol. Other reported promoters are modenite (hydrogen form), water, phosphoric acid, fatty acids (e.g. valeric acid), ketones, organic esters, ethers, polyhydric alcohols, silica gel and the like.

For use as synlubes the oligomer product is preferably a trimer or higher oligomer including mixtures thereof. Low viscosity synlubes are preferably 1-decene trimer. These have a viscosity at 100° C. of about 3.4–3.7 cs (centistokes). By including a small amount (e.g. 2–10 weight percent) of tetramer the viscosity can be increased to a more desirable 3.7–4.1 cs at 100° C.

It has been observed that all 1-decene trimer fractions are not the same even when made with the same catalyst. For example, use of a promoted (e.g. water, alcohol, etc.) $BF_3$ system to oligomerize 1-decene followed by (1) topping to remove monomer and dimer and (2) distillation of the topped oligomer to remove a trimer fraction and (3) hydrogenation of the trimer fraction will give a synlube which either meets or can be adjusted to meet the 4 cs synlube viscosity specifications. However, even though the synlube exhibits the proper viscosity at −40° C. (e.g. 2000–3000 cs) and 100° C. (e.g. 3.6–4.2 cs), the synlube will frequently fail to meet the low temperature pour point specification. A satisfactory 4 cs synlube should have a pour point of −65° C. or lower. Thus a need exists for a method for making an α-olefin synlube that will not only meet the required viscosity specifications but will also consistently exhibit a satisfactory pour point.

SUMMARY OF THE INVENTION

According to the present invention, a process is provided which consistently produces a low pour point synlube by contacting an α-olefin with a $BF_3$ catalyst and feeding a promoter to the α-olefin and $BF_3$ at a slow controlled rate over an extended period of at least one-half hour. The pour point of such a product is substantially lower than that of a similar product made by initially adding all the promoter.

DESCRIPTION OF THE PREFERRED EMBODIMENTS

A preferred embodiment of the invention is a process for making an α-olefin oligomer synlube having a consistently low pour point, said process comprising introducing $BF_3$ into a $C_{8-12}$ α-olefin or mixture of α-olefins and adding a promoter amount of a catalyst promoter to said $C_{8-12}$ α-olefin at a controlled rate over an extended period while maintaining the reaction temperature at about 15°–40° C.

Alpha-olefins useful in the process are those containing about 8–12 carbon atoms. Although mixture of lower olefins, e.g. $C_{6-8}$, with higher olefins, e.g. $C_{12-14}$, can be used. The α-olefins are mainly linear terminal olefins. By far the most preferred olefin is 1-decene.

The process can be conducted by placing the α-olefin in a suitable corrosion-resistant reactor and contacting the olefin with $BF_3$. This can be done in many ways such as by bubbling $BF_3$ through the α-olefin or placing the α-olefin under $BF_3$ pressure (e.g. 10–20 psig) in a closed reactor. A promoter for the $BF_3$ is then slowly added to the reaction mixture at a controlled rate. Any of the known $BF_3$ promoters can be used such as water, alcohol (isopropanol, n-butanol, 1-decanol, etc.), fatty acid (e.g. acetic acid, valeric acid, caproic acid, etc.), organic esters (e.g. butyl acetate, methyl valerate, etc.), ketones (e.g. methyl ethyl ketone, methyl isobutyl ketone, etc.), ethers, alkoxylated alcohols (e.g. 2-ethoxy ethanol, etc.), polyhydric alcohols (e.g. glycol, glycerol, etc.) and the like.

The most preferred promoters are water and alcohols (e.g. n-butanol).

The total amount of promoter added over the extended period should be a promoter amount. This can vary over a wide range, e.g. 0.1–2.0 weight percent based on α-olefin. A preferred promoter amount is about 0.3–1.0 weight percent and a more preferred promoter amount is 0.4–0.8 weight percent. The important thing is that the promoter amount, whatever amount is used, is fed very slowly to the reaction mixture. It is believed that this initially causes some isomerization of the initial oligomerization products before the reaction has proceeded to the trimer-tetramer stage. Then as more promoter is added the reaction proceeds to the trimer-tetramer and higher stage but, because of the isomerization early in the process when very little promoter was present, the product finally obtained will have a very low pour point. This is believed to be due to methyl-branching introduced during the isomerization stage. However, the results achieved by the process do not depend on any knowledge of the exact mechanism of the process.

The following examples will show how the process can be conducted and the results achieved compared to the results obtained by following a conventional process.

EXAMPLES 1-4

These examples are for comparative purposes and are conducted using a conventional procedure.

In an autoclave was placed 1500 g 1-decene and 5.1 g n-butanol promoter. The autoclave was sealed and while stirring pressurized to 20 psig with $BF_3$. The temperature was held at 30° C. After 1.92 hours the autoclave was vented and the reaction mixture washed with water to remove $BF_3$ and n-butanol. The composition of the crude unsaturated oligomer was determined by gas chromatography (GC). The results are shown in Table I.

The reaction mixture was then distilled to remove a monomer-dimer fraction (260° C., 6 torr). Following this a trimer fraction was distilled (298° C., 6 torr). The trimer fraction was then hydrogenated at 200° C. under 400 psig hydrogen using 5% nickel catalyst. Composition was determined by gas chromatography (GC).

The above examples was repeated 3 more times with minor variations to give 4 crude unsaturated oligomers. These variations and the composition of all 4 crude oligomers is shown in the following Table I. Table II shows pertinent physical properties of the hydrogenated trimer fraction obtained from each crude oligomer.

TABLE I

| Example | n-butanol wt % | Rxn Time hrs | Composition[1] (wt. %) | | | | | |
|---|---|---|---|---|---|---|---|---|
| | | | $C_{10}$ | $C_{20}$ | $C_{30}$ | $C_{40}$ | $C_{50}$ | $C_{60}$ |
| 1 | 0.34 | 1.92 | 0.5 | 2.2 | 50.9 | 29.0 | 12.6 | 4.5 |
| 2 | 0.34 | 2.0 | 0.5 | 2.1 | 50.3 | 28.7 | 12.8 | 5.4 |
| 3 | 0.70 | 2.0 | 0.4 | 1.5 | 45.1 | 31.9 | 15.8 | 4.9 |
| 4 | 0.70 | 3.0 | 0.5 | 1.5 | 41.9 | 31.3 | 16.9 | 7.7 |

[1]$C_{10}$, $C_{20}$, $C_{30}$, etc. are monomer, dimer, trimer, etc.

TABLE II

| Example | Viscosity (cs) | | Pour Point (°C.) |
|---|---|---|---|
| | 100° C. | −40° C. | |
| 1 | 3.66 | 2200 | −51 |
| 2 | 3.68 | 2090 | −57 |
| 3 | 3.55 | 2230 | −55 |
| 4 | 3.58 | 2200 | −54 |

These results show that by following a conventional procedure the viscosity properties of the hydrogenated trimer were in the proper range. However, the pour point was unacceptably high. All pour points were above −60° C.

EXAMPLES 5-7

These examples shows the present process and the properties of the resulting synlube.

In an autoclave was placed 2000 g of 1-decene. The autoclave was sealed and pressurized to 20 psig with $BF_3$. The autoclave was sealed and stirred at 30° C. Then n-butanol promoter was added at a controlled rate according to the following schedule.

| Example | Time to Add n-Butanol (min.) | | | | |
|---|---|---|---|---|---|
| | 0.05 wt %[1] | 0.1 wt %[2] | 0.2 wt %[2] | 0.3 wt %[2] | 0.6 wt %[2] |
| 5 | 0 | 15 | 30 | 45 | 120 |
| 6 | 0 | 15 | 30 | 50 | 70 |
| 7 | 0 | 10 | 20 | 45 | 60 |

[1]Added at start.
[2]Cumulative amounts.

A total of 0.6 wt. % n-butanol was added to each of Examples 5-7 with about one-half of that amount being fed in the first 45-50 minutes. Total reaction time was 2.5 hours following which the reaction mixtures were water-washed and analyzed by GC. The compositions are given in Table III.

TABLE III

| Example | Composition (wt %) | | | | | |
|---|---|---|---|---|---|---|
| | $C_{10}$ | $C_{20}$ | $C_{30}$ | $C_{40}$ | $C_{50}$ | $C_{60}$ |
| 5 | 0.8 | 4.8 | 55.6 | 25.3 | 10.4 | 2.8 |
| 6 | 0.9 | 5.2 | 55.5 | 25.2 | 10.3 | 2.7 |
| 7 | 0.8 | 4.7 | 54.2 | 26.0 | 11.1 | 3.1 |

The crude unsaturated oligomers were topped to remove monomer and dimer and then distilled to recover a trimer fraction. The trimer fractions were hydrogenated at 200° C. under 400 psig hydrogen using a nickel catalyst. The physical properties of the final products are given in Table IV.

TABLE IV

| Example | Viscosity (cs) | | Pour Point[1] (°C.) |
|---|---|---|---|
| | 100° C. | −40° C. | |
| 5 | 3.67 | 2110 | <−66 |
| 6 | 3.70 | 2210 | <−66 |
| 7 | 3.64 | 2040 | <−66 |

[1]The lowest temperature obtainable with the apparatus used was −66° C.

The above tests show that the compositions of the crude oligomer made by the conventional process (Examples 1-4) are similar to the compositions of the crude oligomer made by the present process (Examples 5-7). Likewise the −40° C. and 100° C. viscosities of the synlubes made by the conventional process are similar to the viscosities of the synlubes made by the present process. However, the pour points of the synlubes made using the programmed addition of promoter (Examples 5-7) were all much lower than the pour points of the synlubes made by a conventional process. The conventional 4 cs synlubes had pour points in the range of −51° to −57° C. In sharp contrast the synlubes made by the present process all had pour points below −66° C.

A principal object of the present process is to make a hydrogenated 1-decene trimer fraction having a low pour point and suitable for use as a nominal 4 centistoke synlube. However it should be appreciated that the benefits of the process will apply to any α-olefin oligomer made according to the process and need not be limited to 1-decene nor to only trimer. It applies to other $C_{8-12}$ α-olefins and to trimers, tetramers, pentamers and higher oligomers and to mixtures of such oligomers such as trimer-tetramer mixtures and trimer-tetramer-pentamer-hexamer mixtures.

We claim:

1. A process for making an α-olefin oligomer synlube having a consistently low pour point, said process comprising introducing $BF_3$ into an α-olefin selected from the group consisting of $C_{8-12}$ α-olefins and mixtures thereof and adding a promoter amount of a catalyst promoter selected from the group consisting of water, alcohol and mixtures thereof to the resulting reaction mixture at a controlled rate over an extended period of at least 0.5 hour so as to gradually increase the concentration of said promoter in the reaction mixture while maintaining the reaction temperature at about 15°-40° C. and then hydrogenating the resulting reaction product.

2. A process of claim 1 wherein said extended promoter is water.

3. A process of claim 1 wherein said promoter is an alcohol.

4. A process of claim 3 wherein the promoter amount is about 0.1-2.0 weight percent based on the weight of the α-olefin.

5. A process of claim 4 wherein said alcohol is n-butanol.

6. A process of claim 1 wherein said α-olefin is 1-decene.

7. A process of claim 6 wherein said promoter is water.

8. A process of claim 6 wherein said promoter is an alcohol.

9. A process of claim 6 wherein said $BF_3$ is introduced by conducting the process under $BF_3$ pressure.

10. A process of claim 9 wherein said alcohol is n-butanol.

11. A process of claim 10 wherein said temperature is about 20°–35° C.

12. A process of claim 11 wherein said promoter amount is about 0.1–1.5 weight percent based on the weight of said 1-decene.

13. A process of claim 12 wherein said promoter amount is about 0.25–1.0 weight percent based on the weight of 1-decene.

14. A process of claim 13 wherein said extended time is at one hour.

* * * * *